United States Patent [19]

Larkin

[11] 4,247,076
[45] Jan. 27, 1981

[54] TOGGLE ACTION TUBING CLAMP
[75] Inventor: Mark E. Larkin, Lindenhurst, Ill.
[73] Assignee: Abbott Laboratories, North Chicago, Ill.
[21] Appl. No.: 30,258
[22] Filed: Apr. 16, 1979
[51] Int. Cl.³ .............................................. F16K 7/06
[52] U.S. Cl. ..................... 251/7; 24/132 R; 24/255 SL; 251/9
[58] Field of Search .................. 128/346; 251/4, 6, 7, 251/9, 10; 24/129 R, 132 R, 255 SL; 72/451

[56] References Cited
U.S. PATENT DOCUMENTS

| | | | |
|---|---|---|---|
| 758,449 | 4/1904 | Jeralds | 251/10 |
| 827,640 | 7/1906 | Jessup | 251/10 |
| 2,842,331 | 7/1958 | Anderson | 251/6 |
| 2,869,816 | 1/1959 | Olander | 251/6 |
| 2,998,956 | 9/1961 | Etten | 251/10 |
| 3,698,681 | 10/1972 | Lacey | 251/10 |
| 4,053,135 | 10/1977 | Saliaris | 251/10 |
| 4,159,634 | 7/1979 | Stengard | 72/451 X |

Primary Examiner—Harold W. Weakley
Assistant Examiner—Richard Gerard
Attorney, Agent, or Firm—Robert L. Niblack; Neil E. Hamilton

[57] ABSTRACT

A flow control device for flexible tubing wherein the device utilizes a toggle action in compressing the tubing against an anvil surface. A ratchet element is employed in conjunction with the toggle-action clamp to incrementally compress the tubing against the anvil surface. The clamp can be inexpensively molded in one piece and easily assembled without the placement of additional parts in the clamp body. The ratchet and toggle mechanisms offer the advantage of a one-hand operation for incremental compression of the tubing as well as a release of the clamp member.

16 Claims, 4 Drawing Figures

TOGGLE ACTION TUBING CLAMP

BACKGROUND OF THE INVENTION

This invention relates to a flow control device for regulating the flow of fluid through a length of flexible tubing. More particularly, this invention relates to a clamp and flow control member which utilizes a toggle and ratchet mechanism for controlling the flow of liquid through a length of tubing in an intravenous liquid administration set.

Clamping devices or flow control units of the type concerned with in this invention are disclosed in U.S. Pat. Nos. 758,449; 827,640; 2,998,956 and 4,053,135. Toggle-type tubing clamps are described in U.S. Pat. Nos. 2,998,956 and 4,053,145. In U.S. Pat. Nos. 758,449 and 827,640 ratchet-type tubing clamps are described. Nowhere in the prior art is there provided a tubing clamp which utilizes a toggle-action feature in combination with a ratchet mechanism so that an arm member of the clamp can be incrementally forced against the tubing to accurately control fluid flow. Neither does the prior art provide a clamping member of the type previously described which can be easily molded into a single blank and assembled from that blank in a quick and inexpensive manner. The prior art does not offer a combined ratchet and toggle action tubing clamp wherein a single-hand manipulation can afford incremental compression of the tubing to control fluid flow and quick release of the clamp member from the tubing.

It is an advantage of the present invention to provide an inexpensive clamp for controlling flow of fluid through a length of flexible tubing and which can be operated by one hand. Other advantages are a flow control unit which can be fabricated from a single blank of material; does not require the assembly of additional parts; can be fabricated without expensive molding procedures and is disposable.

SUMMARY OF THE INVENTION

The foregoing advantages are accomplished and the shortcomings of the prior art are overcome by the present tubing clamp which has a clamping body defining a base portion with a passageway for the length of tubing. A first arm member is hingedly secured to the base portion and a second arm member presenting a tubing engaging portion is hingedly secured to the first arm member opposite its attachment to the base portion. The tubing engaging portion of the second arm member and the base portion provide guide means to position the tubing engaging portion in contact with the tubing. The guide means is provided by opposite guide tracks carried by the base portion and opposing projections laterally carried by the tubing engaging portion. Ratchet means are operatively associated with the base portion and the arm members to effect incremental movement of the tubing engaging portion against the tubing so as to control liquid flow in the tubing. The ratchet means is provided by a ratchet element extending from the base portion and hinged thereto which is engaged by a surface defined by the first arm member. The tubing clamp is formed as a single blank member extending in a single plane. To assemble the unit, all that is required is for the arm members to be folded by means of hinging portions back over the base portion and the ratchet element to be moved upwardly from the base, passed through an opening in the second arm and in engagement with an end surface in the first arm.

BRIEF DESCRIPTION OF THE DRAWINGS

A better understanding of the clamp and flow control unit of this invention will be accomplished by reference to the drawings wherein.

DESCRIPTION OF THE PREFERRED EMBODIMENT

Figure 1:
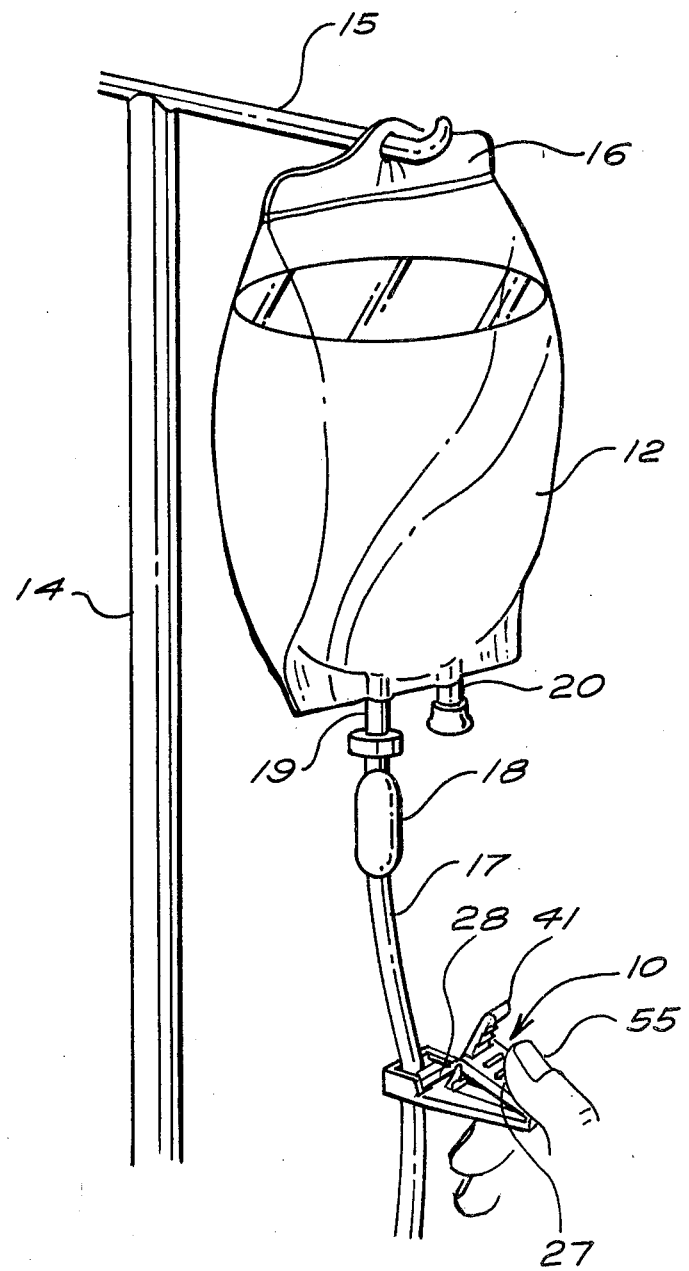
FIG. 1 is a perspective view illustrating the flow control clamp member operatively associated with a parenteral administration unit.

Proceeding to a detailed description of a preferred embodiment of the present invention, the flow control device, generally 10 is shown in conjunction with a parenteral administration unit composed of a flexible solution container 12 which is supported by means of a support device 14 having an arm 15 extending through flap 16. A combined drip chamber and piercing pin 18 extends through administration port 19 in a fluid-tight manner and in communication with the contents of bag 12. The usual additive port 20 is also provided in solution container 12.

Figure 2:
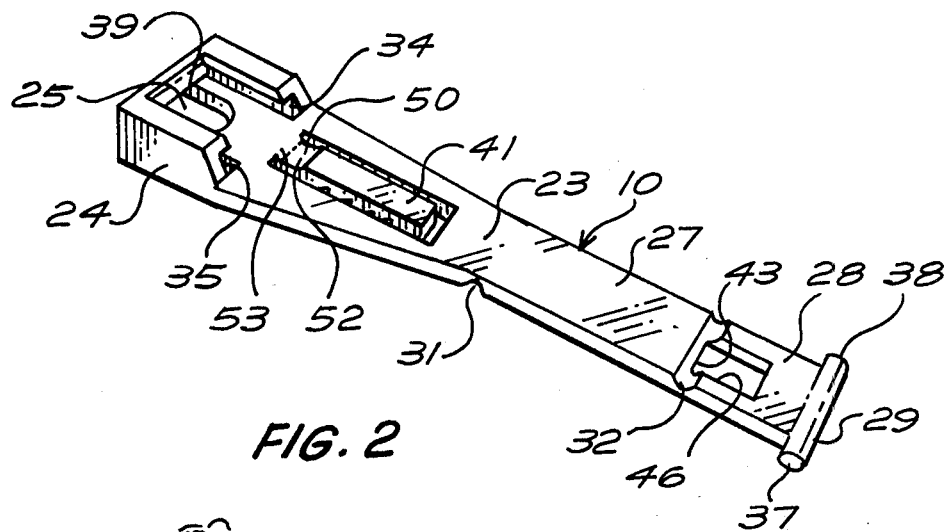
FIG. 2 is a perspective view showing the clamp unit of this invention in the form it would be immediately after molding.
Figure 3:
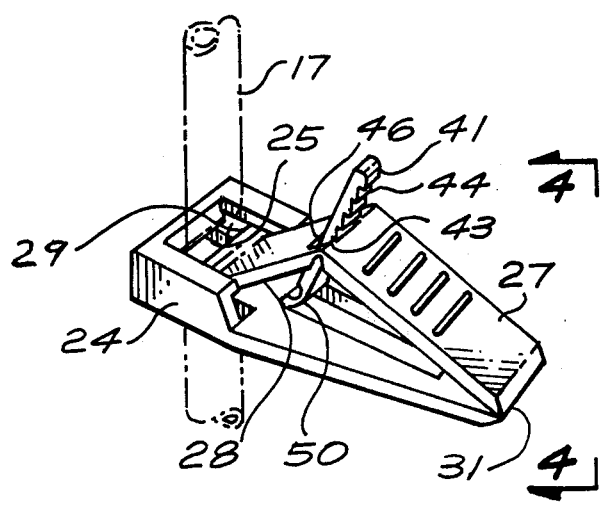
FIG. 3 is a perspective view showing the clamp unit of this invention with a length of tubing extending therethrough and in an assembled condition during operation.

As best shown in FIG. 2, the combined flow control and clamp device 10 has a clamp body 23 composed of a base portion 24 through which extends a C-shaped passageway 25. A first arm 27 is attached to base portion 24 by means of a hinge section 31. Extending from first arm 27 is a second arm 28 which likewise is attached by means of a hinge section 32. A tubing engaging portion 29 is provided at the end of second arm 28 and opposite its attachment to first arm 27. Projections 37 and 38 extend laterally from tubing engaging portion 29. These projections are dimensioned so as to fit within guide tracks 35 and 34 provided in base portion 24 and adjacent passageway 25. It will be further noted that disposed within base portion 24 and hingedly secured thereto is a ratchet element 41 which is attached to base portion 24 by means of a hinge 50. An opening 46 is provided in second arm 28 and defined in part by surface 43 of arm 27 so that ratchet element 41 can extend through arm 28 when the clamp is in an assembled condition such as shown in FIG. 3.

Tubing clamp 10 can be easily injection molded from a resinous plastic material such as polypropylene and when released from the mold will be in the form of a one piece, rigid blank extending in a single plane as shown in FIG. 2. In this condition it should be noted that there will be provided opposing V-shaped hinges 31 and 32 which hinge first arm 27 to the base portion 24 and the second arm 28 to the first arm. Also, it should be noted that a flap-type hinge 50 secures ratchet element 41 to base portion 24 and is constructed in a manner so that it is curved upwardly from the horizontal plane of the clamp such as indicated by the numeral 52 as shown in FIG. 2 and is directly secured to the base portion 24, and formed as a part thereof, by means of a securing section 53 to thus provide a flap-type hinge with a bias toward base 24. To assemble clamp 10 all that is required is for the first arm 27 to be moved in a counterclockwise motion as viewed in FIG. 2 and over base portion 24. This is effected by means of hinge 31. At the same time, projections 37 and 38 will be inserted into guide tracks 35 and 34. This is aided by the pivoting of arm 28 with respect to arm 27 as afforded by hinge 31. Ratchet element 41 will then be moved upwardly to extend through opening 46 so that teeth 44 will engage engagement surface 43 on the first arm 27. The clamp will then assume a position shown in FIG. 3.

OPERATION

Figure 4:
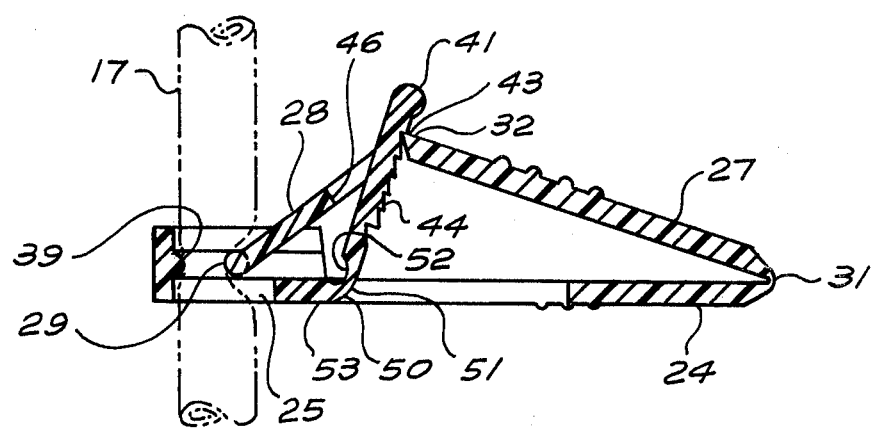
FIG. 4 is a view in vertical section taken along line 4—4 of FIG. 3.

A better understanding of the advantages of flow control device 10 will be had by a description of its operation. Tubing clamp 10 will be supplied as a component part of an I.V. administration set as shown in FIG. 1 with tubing 17 positioned through passageway 25. The tubing engaging portion 29 can be spaced from tubing 17 or in slight contact with it for positioning purposes as best illustrated in FIG. 3. When it is desired to control the flow of liquid through tubing 17 all that is required is a force to be exerted on first arm 27 so as to move arm 27 in the direction of base 24 whereby projections 37 and 38 will ride in tracks 35 and 34 and tubing engaging portion 29 will compress tubing 17 against anvil surface 39. As first arm 27 is moved in the direction of base 24, engaging surface 43 of arm 27 will ride over ratchet teeth 44 so as to incrementally move tubing engaging portion 29 against tubing 17. The resilient force of tubing 17 against tubing engaging portion 29 in an opposing direction will tend to move arms 27 and 28 upwardly and away from base 24. This opposing movement will be limited by means of the biasing of ratchet element 41 in the direction of arm 27 and engagement of surface 43 against teeth 44. Consequently, the tubing engaging portion 29 will remain in a stationary manner and against tubing 17 when force such as by means of a thumb 55 is released from arm 27. This is best seen in FIG. 4. To stop the flow in tubing 17, arm 27 is moved in the direction of base 24 until the opposing walls of tubing 17 are compressed between tubing engaging portion 29 and anvil surface 39. To release the force of tubing engaging portion 29 from tubing 17 all that is required is a movement of ratchet element 41 in a direction away from arm 27 and surface 43. The resilient force of tubing 17 on engagement portion 29 will then cause arm 28 to move away from the tubing and arm 28 to ride upwardly along ratchet element 41 through opening 46.

An important feature of this invention is the utilization of hinge 50 which by its design will effect a biasing force on the ratchet element 41 and in the direction of base 24 so that at all times during the operation of the clamp, it will contact the engagement surface 43 of first arm 27. Also, it should be appreciated that the hinging of the arms to themselves as well as to the base 24 is also important. This is especially true concerning the hinge section 31 in that when the clamp is in the assembled condition as shown in FIG. 3, this hinge through its plastic memory will tend to exert a force away from base 24 so that even if tubing 17 is not placed in passageway 25, tubing engaging portion 29 will move away from passageway 25. The construction of hinge 32 will also aid in this upward movement.

It will be appreciated that the foregoing hinging action of the arm members as well as the biasing of ratchet element 41 are all accomplished in a single injection molding operation and without the need for close tolerances or subsequent assembly of parts. It will be recognized that while teeth 44 have been shown in conjunction with ratchet element 41 any type of a projecting-type surface could be utilized so long as it will engage with first arm 27. Similarly, while a beveled engaging surface 43 is utilized in connection with arm 27 to result in a knife edge for engagement with teeth 44, any type of projecting surface which will effect intermittent contact with ratchet element 41 could be utilized. An anvil surface 39 is shown in conjunction with base 24 for purposes of forming a constricting surface when tubing engaging portion 29 acts against the opposing wall of tubing 17. This is not essential and while promoting a more efficient operation, could be eliminated. It will be further seen that the hinge sections 31 and 32 are formed in a generally V-shaped configuration and are oppositely disposed. Any geometric configuration could be utilized so long as the hinging action is effected and an upwardly biasing effect is accomplished when the clamp is in the assembled condition. Further, while guide tracts 34 and 35 preferably extend over one-third of the longitudinal distance of the base portion, this is not essential and could be of varying proportion.

The preferred plastic material for molding clamp 10 is polypropylene. However, other plastic materials such as polyethylene could be employed. While injection molding is stated as the preferred method for fabricating clamp 10 other methods such as rule die cutting could be utilized.

It will thus be seen that through the present invention there is now provided a flow control clamp which can control the flow of liquid in a length of flexible tubing by means of a clamp member which is inexpensive to fabricate. No assembly of additional components is required but merely the bending of the arm sections and the placement of one component within another component which is already formed as a part of the clamp. The clamp unit of this invention is easily operated with one hand yet can be disengaged by a mere movement of a ratchet element. Incremental flow control can be accomplished or complete shutoff of flow by the same unit. All of the foregoing advantages are provided in a tubing clamp which by means of its fabrication is disposable, thus being particularly adapted for use with an I.V. administration set.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:
1. A tubing clamp for regulating flow through a length of flexible tubing comprising:
   (a) a clamping body defining a base portion with a passageway for said length of tubing;
   (b) a first arm member hingedly secured to said base portion;
   (c) a second arm member presenting a tubing engaging portion and hingedly secured to said first arm member at a position opposite the securing of said first arm member to said base portion;
   (d) guide means operatively associated with said tubing engaging portion of said second arm member and said base portion adjacent said passageway to position said tubing engaging portion in contact with said tubing; and (e) ratchet means operatively associated with said base portion and said arm members to effect incremental movement of said tubing engaging portion against said tubing.

2. The tubing clamp as defined in claim 1 wherein said ratchet means includes a ratchet element extending from said base portion and a surface defined by said first arm member for engagement with said ratchet element.

3. The tubing clamp as defined in claim 2 wherein said ratchet element is defined by a toothed member and said second arm member has an opening to permit a portion of said element to pass therethrough.

4. The tubing clamp as defined in claim 3 wherein said surface for engagement with said ratchet element is defined by a beveled edge positioned adjacent the hinging of said first and second arm members and said opening in said second arm member.

5. The tubing clamp as defined in claim 4 wherein said ratchet element is hingedly attached to said base portion and biased toward said beveled edge of said first arm member.

6. The tubing clamp as defined in claim 1 wherein said guide means is defined by opposing guide tracks carried by said base portion and opposing projections laterally carried by said tubing engaging portion.

7. The tubing clamp as defined in claim 6 wherein said clamping body further includes an anvil surface positioned adjacent said passageway and opposite said tubing engaging portion of said second arm member.

8. The tubing clamp as defined in claim 7 wherein said passageway is of a generally C-shaped configuration with said anvil surface located at the widest portion of the passageway.

9. The tubing clamp as defined in claim 8 wherein said guide means of said base portion extends over approximately one-third of the longitudinal distance of said base portion.

10. A one-piece ratchet-type tubing clamp for regulating flow through a length of flexible tubing comprising:

(a) a clamping body defining a base portion with a passageway for said length of tubing;
(b) a first arm member integrally and hingedly attached to said base portion;
(c) a second arm member presenting a tubing engaging portion integrally and hingedly attached to said first arm member at a position opposite the securing of said first arm member to said base portion;
(d) guide track means defined by said base portion adjacent said passageway;
(e) projections extending laterally from said second arm member adjacent said tubing engaging portion for slidable engagement in said guide track means;
(f) a ratchet bar element having teeth extending therefrom integrally and hingedly secured to said base portion; and
(g) an opening in said second arm member defined in part by an engaging surface carried by said first arm member for passage of said ratchet bar through said opening and contact of said engaging surface with said teeth of said ratchet bar.

11. The one-piece ratchet-type tubing clamp as defined in claim 10 wherein said base portion and said arm members initially formed as a one-piece blank extending in a single plane.

12. The one-piece ratchet-type tubing clamp as defined in claim 11 wherein said first arm member is hinged to said base portion and said second arm member is hinged to said first arm member by means of generally V-shaped grooves which are oppositely disposed.

13. The one-piece ratchet-type tubing clamp as defined in claim 12 wherein said hinge securing said ratchet bar element to said base is defined by an integral flap section.

14. The one-piece ratchet-type tubing clamp as defined in claim 13 wherein said tubing clamp is formed from a rigid plastic material.

15. The one-piece ratchet-type tubing clamp as defined in claim 13 wherein said ratchet bar element is initially formed as a portion of said base portion.

16. The one-piece ratchet-type tubing clamp as defined in claim 14 wherein said plastic material is polypropylene.

* * * * *